US006676966B1

(12) United States Patent
Odidi et al.

(10) Patent No.: US 6,676,966 B1
(45) Date of Patent: *Jan. 13, 2004

(54) EXTENDED RELEASE METFORMIN HYDROCHLORIDE FORMULATIONS

(75) Inventors: Amina Odidi, Toronto (CA); Isa Odidi, Toronto (CA)

(73) Assignee: Intellipharmaceutics Corp., Mississauga (CA)

( * ) Notice: Subject to any disclaimer, the term of this patent is extended or adjusted under 35 U.S.C. 154(b) by 193 days.

This patent is subject to a terminal disclaimer.

(21) Appl. No.: 09/845,496

(22) Filed: May 1, 2001

Related U.S. Application Data

(60) Provisional application No. 60/202,768, filed on May 9, 2000.

(51) Int. Cl.[7] .............................. A61K 9/22; A61K 9/36; A61K 9/54
(52) U.S. Cl. ........................ 424/464; 424/469; 424/468; 424/484; 424/489; 424/450; 424/456; 424/475; 424/479; 424/480; 424/474; 424/472
(58) Field of Search .................................. 424/464, 472, 424/473, 468, 474, 475, 479, 480

(56) References Cited

U.S. PATENT DOCUMENTS

| 4,351,825 | A | | 9/1982 | Sothmann et al. |
| 4,834,985 | A | | 5/1989 | Elger et al. |
| 5,055,306 | A | | 10/1991 | Barry et al. |
| 5,540,665 | A | | 7/1996 | Mercado et al. |
| 5,575,987 | A | | 11/1996 | Kamei et al. |
| 5,576,306 | A | | 11/1996 | Dressman et al. |
| 5,594,091 | A | | 1/1997 | Igari et al. |
| 5,955,106 | A | * | 9/1999 | Moeckel et al. ............. 424/464 |
| 6,039,975 | A | | 3/2000 | Shah et al. .................. 424/473 |
| 6,099,859 | A | * | 8/2000 | Cheng et al. ................ 424/464 |
| 6,296,876 | B1 | * | 10/2001 | Odidi et al. ................. 424/480 |
| 6,312,724 | B1 | * | 11/2001 | Odidi et al. ................. 424/468 |
| 6,479,075 | B1 | * | 11/2002 | Odidi et al. ................. 424/458 |
| 6,509,037 | B2 | * | 1/2003 | Odidi et al. ................. 424/468 |

OTHER PUBLICATIONS

U.S. patent application Ser. No. PCT/US99/19978, no date.

* cited by examiner

Primary Examiner—Sabiha Qazi
(74) Attorney, Agent, or Firm—Sim & McBurney

(57) ABSTRACT

An extended release formulation of metformin hydrochloride is disclosed. The metformin hydrochloride is encased within polymeric film layers providing for gradual release of the metformin hydrochloride for over 12 and even 24 hours in the gastrointestinal tract and the blood plasma.

13 Claims, No Drawings

EXTENDED RELEASE METFORMIN HYDROCHLORIDE FORMULATIONS

RELATED APPLICATIONS

This application claims priority to U.S. application Ser. No. 60/202,768 filed May 9, 2000.

FIELD OF THE INVENTION

The present invention relates mainly to a formulation composition and method of producing extended release dosage form containing metformin hydrochloride or a pharmaceutically acceptable salt thereof.

BACKGROUND OF THE INVENTION

Metformin hydrochloride is an oral antihyperglycemic drug used in the management of non-insulin-dependent diabetes mellitus (type 2 diabetes). Metformin hydrochloride, as monotherapy, is indicated as an adjunct to diet to lower blood glucose in patients with type 2 diabetes whose hyperglycemia cannot be satisfactorily managed on diet alone. Recommended dosing schedule for metformin involves dose escalation with each dose given with meals. This allows metformin to be better tolerated as gastrointestinal symptoms usually associated with metformin therapy may be minimized. However it has been reported in the Physician Desk Reference electronic library release 2000.1 that, food decreases the extent and slightly delays the absorption of metformin, as shown by approximately a 40% lower peak concentration and 25% lower AUC in plasma and a 35 minute prolongation of time to peak plasma concentration following administration of a single 850 mg immediate release tablet of metformin with food, compared to the same tablet strength administered without food. Metformin is marketed as an immediate release formulation and is administered several times a day a situation that has raised concerns regarding patient compliance.

Limited research work has been done to fabricate controlled release metformin hydrochloride and no successful work has been reported on an extended release metformin composition or dosage form.

A pharmaceutical preparation containing metformin and a process for producing it is disclosed in U.S. Pat. No. 5,955,106 in which the pharmaceutical compositions contain metformin as an active substance and a hydrocolloid-formning agent as a retardant. The invention also concerns a process in which the active substance and retarding agent or a portion thereof are granulated with an aqueous solvent optionally containing a binder and where appropriate the other portion of the retardant or other standard pharmaceutical auxiliaries are admixed with the granulate.

U.S. Pat. No. 5,594,091 discloses a matrix for sustained-release preparation comprising an ester formed at a terminal carboxyl group of a straight-chain polyester which essentially consists of an alpha-hydroxymonocarboxylic acid.

U.S. Pat. No. 5,576,306 discloses pharmaceutical compositions and uses of water-soluble, high-viscosity grade cellulose ethers which may be in the form of a prehydrated ingestible composition, such as a gelatin, or a comestible, such as a cookie.

U.S. Pat. No. 5,575,987 discloses a method of producing sustained-release microcapsules from an WIO emulsion comprising an inner aqueous phase containing said metformin and an external oil phase containing a biodegradable polymer.

U.S. Pat. No. 5,540,665 discloses a gas driven dispensing device and gas generating engine comprising (a) a solid composition comprising an acidic compound or a basic compound, or a combination thereof, and (b) a means for maintaining substantially constant the surface area of the solid composition exposed to a reservoir fluid comprising water, or water and an acidic compound, or water and a basic compound, wherein in operation, the solid composition is exposed to the reservoir fluid which dissolves the solid composition and causes it to generate a gas, the gas being a driving fluid to dispense a beneficial agent such as metformin.

U.S. Pat. No. 5,055,306 discloses a granular sustained-release formulation consisting of a pharmacologically active substance presented in the form of a tablet, said tablet comprising sufficient granules to provide a predetermined dose or number of doses of the pharmacologically active substance and effervescent or water-dispersible ingredients, each of said granules having a diameter of preferably between 0.5 and 2.5 mm and comprising: a) a core comprising one or more pharmacologically active substances and preferably one or more excipients; and b) a coating covering substantially the whole surface of the core and comprising 100 parts of a water insoluble but water swellable acrylic polymer and from 20 to 70 parts of a water soluble hydroxylated cellulose derivative, the weight of the coating being from 2 to 25% of the weight of the core. A method for preparing this effervescent of water-dispersible tablet formulation is also provided.

U.S. Pat. No. 4,834,985 discloses a solid controlled release pharmaceutical composition comprising an active ingredient incorporated in a matrix comprising a first substance selected from a water soluble polydextrose and a water soluble cyclodextrin and a second substance selected from a $C_{12}$–$C_{36}$ fatty alcohol and a polyalkylene glycol. Preferably the first substance is a cyclodextrin, especially a beta-cyclodextrin, while the second substance is a $C_{14}$–$C_{22}$ fatty alcohol, especially stearyl alcohol, cetyl alcohol, cetostearyl alcohol or myristyl alcohol. The matrix may also contain a cellulose ether, especially a hydroxyalkylcellulose or a carboxyalkylcellulose.

U.S. Pat. No. 4,351,825 discloses a process for the preparation of matrix-type tablets with retarded liberation of the active agent. In the granulation process, polymethacrylate plastics insoluble in neutral or slightly acid water either as dissolved in an organic solvent or as a water dispersion are used as the retarding matrix substance. Before the tablets are compressed, an ester of a large-molecule fatty acid or a product obtained from same by means of hydrogenation is mixed into the grain mix in order to adjust the rate of liberation of the active agent.

PCT/US99/19978 discloses a controlled release pharmaceutical tablet containing antihyperglycemic drug and a hypoglycemic drug comprising a core containing the antihyperglycemic drug, a semipermeable coating membrane surrounding the core and at least one passageway in the membrane to allow the drugs to be released from the core.

The problem with current controlled release formulations of metformin is that the extent of metformin release or bioavailability is not optimal or does not provide sufficient coverage over an extended period of time such as for 12 hours and a 24 hour period. Furthermore, for coated tablets the choice of coating polymer(s) makes large scale or commercial production of consistent and reproducible batches difficult if not impossible. The manufacturing process for these formulations involves long process times and a large number of process steps, requiring qualification, cleaning and validation. Stability problems during manufacture and storage may be an issue with current controlled systems especially for the delivery of large doses of metformin.

SUMMARY OF THE INVENTION

It is an object of the present invention to provide an extended and controlled release composition and formulation of metformin hydrochloride that can provide detectable blood levels of the said agent over 12 hours and or over 24 hours when given to humans or animals thus allowing for twice and/or once daily administration.

It is also an object of the present invention to provide an extended and controlled release composition and formulation of metformin hydrochloride that does not employ a matrix-type tablet or contain an expandable, gelling, swellable hydrocolloid polymer as a retardant agent.

It is a further object of the present invention to provide an extended and controlled release composition and formulation of metformin hydrochloride that does not employ sustained-release microcapsules.

It is a further object of the present invention to provide an extended and controlled release composition and formulation of metformin hydrochloride that does not employ a gas driven dispensing device and gas generating engine to dispense a beneficial agent such as metformin.

It is also a further object of the present invention to provide an extended and controlled release composition and formulation of metformin hydrochloride that is not a granular sustained-release formulation of effervescent water-dispersible tablet.

It is a further object of the present invention to provide an extended and controlled release composition and formulation of metformin hydrochloride that is not a controlled release pharmaceutical tablet comprising a core containing the metformin hydrochloride, a semipermeable coating membrane surrounding the core with passageway(s) in the membrane.

It is also an object of the present invention to provide an extended and controlled release composition and formulation of metformin hydrochloride in which the rate of input and the extent of release (bioavailability) of the agent is reduced compared to an immediate release formulation of same dosage strength when administered under fasting condition but increased or remain unchanged when given with food.

It is also an object of the present invention to provide an extended and controlled release composition and formulation of metformin hydrochloride in which there is a lag phase before the gradual release of the agent is begun in which the timing, rate and extent of drug release is pH dependent.

According to an aspect of the present invention there is provided an extended release metformin hydrochloride formulation comprising: metformin hydrochloride; and an encasement coat in the form of one or more layers of pH sensitive polymeric film encasing said metformin hydrochloride; wherein said polymeric film is soluble in a pH of about above 5.0. The metformin hydrochloride may be provided in the form of a capsule, pellet or bead which is encased with a polymeric film.

According to a further aspect of the present invention is an extended release metformin hydrochloride formulation comprising: (a) a capsule, tablet, pellet or bead of metformin hydrochloride comprising about 5–95% by weight metformin hydrochloride; about 0–60% by weight pharmaceutical compression aid; and about 0–50% by weight pharmaceutical extrusion aid; and (b) an encasement coat in the form of one or more layers of a pH sensitive polymeric film encasing said capsule, tablet, pellet or bead, said encasement coat comprising about 5–55% by weight polymer; and about 0.5–30% by weight plasticizer; wherein said polymeric film is soluble above a pH of about 5.0. The polymeric films used in the formulations of the present invention are insoluble in acid media and dissolve by salt formation in a pH above about 5.0.

According to still another aspect of the present invention is a method for making an extended release metformin hydrochloride formulation comprising: compressing metformin hydrochloride into tablets, pellets or beads; encasing said tablets, pellets or beads in an encasement coat in the form of one or more layers of a pH sensitive polymeric film, said encasement coat comprising about 5–55% by weight polymer; and about 0.5–30% by weight plasticizer; wherein said polymeric film is soluble above a pH of about 5.0.

DETAILED DESCRIPTION OF THE PREFERRED EMBODIMENTS

Through intensive investigation to resolve the above problems and achieve the foregoing aspects and objectives, the Applicants found it surprisingly possible to produce extended and controlled release composition and formulation containing metformin hydrochloride presented in the form of (1) a non gas driven, non hydrogelling, non swelling or non matrix tablet made by dry granulation or direct compression of the metformin hydrochloride; (2) the metformin tablet is encased in one or more layers of pH solubility dependant polymeric film(s) (a) which is not semipermeable, non permeable, non swellable and has no passage way; and (b) which is insoluble in acid media and dissolve by salt formation above pH 5–6.

Surprisingly, the present invention when ingested in the presence of food is capable of providing more than 12 hours and or more than 24 hours of delivery of the metformin hydrochloride in the gastrointestinal tract and blood plasma without a decrease in the extent of release or bioavailability.

The present invention is an extended release metformin hydrochloride formulation that comprises metformin hydrochloride that can be in the form of a capsule, tablet, pellet or bead which is encased with an encasement coat in the form of one or more layers of a pH sensitive polymeric film that is soluble above a pH of about 5.0. The capsule, tablet, pellet or bead of metformin hydrochloride comprises about 5–95% by weight metformin hydrochloride, optionally about 0–60% by weight pharmaceutical compression aid, and optionally about 0–50% by weight of a pharmaceutical extrusion aid. The pharmaceutical compression aid may be selected from the group consisting of microcrystalline cellulose, lactose, cellulose, dibasic calcium phosphate dihydrate, calcium sulfite dihydrate, tricalcium phosphate and compressible sugar. The capsule, tablet, pellet or bead of metformin hydrochloride may optionally comprise excipients, lubricants, binders or glidants.

The encasement coat comprises about 5–55% by weight polymer and about 0.5–30% by weight plasticizer. The encasement coat may be a polymeric film which is a polymer selected from the group consisting of cellulose esters, polyvinyl acetate phthalate, methacrylic acid copolymer type A, methacrylic acid copolymer type B, methacrylic acid copolymer type C and any mixtures thereof The encasement coat may be a polymeric film composed of shellac or zein.

The present invention further provides a method for making metformin tablets preferably by dry granulation or direct compression and encasement of the tablet in at least one layer of pH sensitive polymeric film(s). Dry granulation can be accomplished by slugging. The tablet may also be made by first processing metformin alone or with suitable excipients via wet granulation or fluid bed granulation or spray drying before tabletting. To the tablet is optionally added 0–60 % by weight of one or more pharmaceutical compression aids such as microcrystalline cellulose, lactose, cellulose, dibasic calcium phosphate dihydrate, calcium sulfite dihydrate, tricalcium phosphate, and compressible sugar which have high compactibility, good flowability and blending properties and good stability. The tablet may contain lubricants, binders or glidants.

The polymeric film(s) are applied to the metformin hydrochloride being composed of 5 to about 55% of cellulose esters or polyvinyl acetate phthalate or methacrylic acid copolymer type A or methacrylic acid copolymer type B or methacrylic acid copolymer type C or any mixture there of. The polymeric film displays pH sensitive solubility such that it is insoluble in acid medium but soluble in alkaline medium. The polymeric film(s) may be replaced by shellac or Zein. The polymeric film(s) may contain plasticizers, antitacking agents, colorants and metformin hydrochloride.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

The examples are described for the purposes of illustration and are not intended to limit the scope of the invention.

Methods of chemistry, biochemistry and pharmacology referred to but not explicitly described in this disclosure and examples are reported in the scientific literature and are well known to those skilled in the art.

Example 1

An extended release tablet of Metformin hydrochloride containing either 500 mg, 850 mg or 1000 mg was prepared according to the present invention as follows:

1(a) Manufacture of the non-encased tablets or pellets

|  | Formulation A | Formulation B |
| --- | --- | --- |
| Metformin hydrochloride | 80.0% | 45.5% |
| Microcrystalline cellulose | 19.0% | 54.0% |
| Magnesium stearate | 1.0% | 0.5% |

The metformin and silicon dioxide were mixed in a high shear mixer. The mixture was discharged into a v-blender to which was added microcrystalline cellulose and magnesium stearate. The mixture in the v-blender was blended until a homogeneous blend was obtained. The mixture in the v-blender was discharged after blending and compressed into tablets or pellets or beads. The pellets or beads can be manufactured by extrusion spheronization in which a wet mass of the composition is extruded alone or with aid of extruding aids and spheronized.

1(b) Dissolution testing of non-encased tablets or pellets or beads The non-encased tablets or pellets or beads were tested in degassed water.

| Dissolution Time | medium: Degassed water Amount dissolved |
| --- | --- |
| 1 hr | >80% |

1(c) Manufacture of encasement dispersion

|  | Formulation 1 | Formulation 2 |
| --- | --- | --- |
| Methacrylic acid copolymer type A | 12.5% | — |
| Methacrylic acid copolymer type B | — | 10.0% |
| Polyethylene glycol 600 | 1.0% | 1.5% |
| Talc | 3.5% | 3.0% |
| Water and/or Ethanol quantity sufficient | 100.0% | 100.0% |

Polyethylene glycol was added to an aqueous dispersion of methacrylic acid copolymer(s) and mixed. Talc was added while stirring with a propeller mixer. Polyethylene glycol is used as a plasticizer to help enhance the elasticity of the film(s)

[40] 1(d) Application of the Encasement Film(s) and Manufacture of Encased Tablets or Pellets The non-encased tablets or pellets or beads were charged into a perforated coating pan in a pan coater. The inlet air temperature was adjusted so as to have tablet bed temperature at 30° C. Pan speed was set at between 6 and 10 rpm. The spray rate for applying the film(s) on a continuous basis was 3g per minute per kg tablets. The atomization pressure was from 1.5 to about 4 bar. A coating level of about 0.5 to 15 mg of polymer per square centimeter of tablet surface area and preferably 3 to 7 mg/cm2 was applied. Beads may also be coated using a fluid bed dryer.

[41] 1(e) Dissolution Testing of Encased Tablets

The present invention (encased tablets) were tested in Gastric fluid, simulated TS, and Intestinal fluid, simulated TS in accordance to USP 23/NF 18.

| Dissolution simulated Time | medium: Gastric fluid, Amount dissolved | Dissolution simulated Time | Medium: Intestinal fluid, Amount dissolved |
| --- | --- | --- | --- |
| 1 hr | <10% | 1 hr | >80% |

What is claimed is:

1. An extended release metformin hydrochloride formulation comprising:
   metformin hydrochloride; and
   an encasement coat in the form of one or more layers of pH sensitive polymeric film of about 5 up to less than 50% by weight polymer for encasing said metformin hydrochloride; wherein said polymeric film is soluble in a pH of about above 5.0.

2. The formulation of claim 1, wherein said metformin hydrochloride is present in an amount of about 5–95% by weight.

3. The formulation of claim 2, wherein said metformin hydrochloride is provided as a capsule, tablet or pellet.

4. The formulation of claim 3, wherein said capsule, tablet or pellet of metformin hydrochloride additionally comprises an aid selected from the group consisting of a pharmaceutical compression aid, a pharmaceutical extrusion aid and mixtures thereof.

5. The formulation of claim 4, wherein said pharmaceutical compression aid is selected from the group consisting of microcrystalline cellulose, lactose, cellulose, dibasic calcium phosphate dihydrate, calcium sulfite dihydrate, tricalcium phosphate and compressible sugar.

6. The formulation of claim 5, wherein said compression aid is present in an amount of up to about 60% by weight.

7. The formulation of claim 4, wherein said extrusion aid is present in an amount of up to about 50% by weight.

8. The formulation of claim 4, wherein said formulation additionally comprises excipients, lubricants, binders or glidants.

9. The formulation of claim 1, wherein said polymeric film is a polymer selected from the group consisting of cellulose esters, polyvinyl acetate phthalate, methacrylic acid copolymer type A, methacrylic acid copolymer type B, methacrylic acid copolymer type C and any mixtures thereof.

10. The formulation of claim 1, wherein said polymeric film comprises shellac or zein.

11. The formulation of claim 1, wherein said polymeric film further comprises an agent selected from the group consisting of plasticizers, antitacking agents, colorants and mixtures thereof.

12. The formulation of claim 11, wherein said plasticizer is polyethylene glycol.

13. The formulation of claim 12, wherein said antitacking agent is talc.

* * * * *